(12) United States Patent
Opitz et al.

(10) Patent No.: US 9,557,266 B2
(45) Date of Patent: Jan. 31, 2017

(54) SURFACE PLASMON RESONANCE SENSOR

(75) Inventors: Jorg Opitz, Dresden (DE); Jurgen Schreiber, Dresden (DE); Tatiana Gubarevich, Minsk (BY); Victoria Lapina, Minsk (BY); Vladimir Belyi, Minsk (BY); Nikolai Kazak, Minsk (BY); Michael Kroening, Saarbrucken (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 230 days.

(21) Appl. No.: 13/147,946

(22) PCT Filed: Feb. 8, 2010

(86) PCT No.: PCT/EP2010/000769
§ 371 (c)(1),
(2), (4) Date: Dec. 30, 2011

(87) PCT Pub. No.: WO2010/089147
PCT Pub. Date: Aug. 12, 2010

(65) Prior Publication Data
US 2012/0088229 A1    Apr. 12, 2012

(30) Foreign Application Priority Data
Feb. 6, 2009 (EP) .................. 09001679

(51) Int. Cl.
*G01N 21/552* (2014.01)
*G01N 33/543* (2006.01)

(52) U.S. Cl.
CPC ...... *G01N 21/554* (2013.01); *G01N 33/54373* (2013.01); *Y10T 436/143333* (2015.01)

(58) Field of Classification Search
CPC .......................... H01F 1/0036; C01B 31/0484
See application file for complete search history.

(56) References Cited

U.S. PATENT DOCUMENTS

2002/0119255 A1* 8/2002 Divigalpitiya et al. ...... 427/421
2007/0117151 A1  5/2007 Frederix et al.
2008/0038830 A1  2/2008 Ure et al.

FOREIGN PATENT DOCUMENTS

WO   WO-2005/090954 A1   9/2005
WO   WO-2008/130735 A1   10/2008

OTHER PUBLICATIONS

Rong et al., Nanoscale porous silicon waveguide for label-free DNA sensing, Available: Jan. 24, 2008, Biosensors and Bioelectronics, vol. 23, Issue 10, pp. 1572-1576.*
"International Application No. PCT/EP2010/000769, International Preliminary Report on Patentability mailed Aug. 9, 2011", (Aug. 9, 2011), 7 pgs.
"European Application Serial No. 09001679.1, Search Report dated Jul. 17, 2009", (Jul. 17, 2009), 6 pgs.
(Continued)

*Primary Examiner* — Rebecca Martinez
(74) *Attorney, Agent, or Firm* — Schwegman Lundberg & Woessner, P.A.

(57) ABSTRACT

The application relates to a sensor using a gold layer (3) with embedded nanodiamonds (2) on which surface plasmon resonance (SPR) is used to detect target molecules (5).

14 Claims, 3 Drawing Sheets

(56) References Cited

OTHER PUBLICATIONS

"International Application No. PCT/EP2010/000769, International Search Report and Written Opinion mailed Jun. 4, 2010", (Jun. 4, 2010), 15 pgs.

Krueger, A., "New carbon materials: biological applications of functionalized nanodiamond materials", Chemistry, 14(5), (2008), 1382-90.

* cited by examiner

SURFACE PLASMON RESONANCE SENSOR

PRIORITY CLAIM TO RELATED APPLICATIONS

This application is a national stage application under 35 U.S.C. §371 of PCT/EP2010/000769, filed Feb. 8, 2010, and published as WO 2010/089147 A8 on Aug. 12, 2010, which claims priority to European Application No. 09001679.1, filed Feb. 6, 2009, which applications and publication are incorporated herein by reference and made a part hereof in their entirety, and the benefit of priority of each of which is claimed herein.

The invention relates to a sensor using a gold layer with embedded nanodiamonds on which surface plasmon resonance (SPR) is used to detect target molecules.

The invention can be used as a biological sensor, for example for quantitative measurement of antibodyantigen interaction, or as a chemical sensor, for example to monitor the progress of reaction between a sample and target molecule bound to the nanodiamonds. The present invention uses a coupling of the targetmolecules to in the gold layer embedded functionalized nanodiamonds. This binding can be done by all possible interconnections provided from carbon chemistry. The coupling to the surface plasmon-polariton of the gold layer is realized due to the strong scattering of the nanodiamonds. In comparison to established SPR sensors, where the binding of the antibody, antigen or chemical is realized by a multilayer technology on top of the sensing gold layer, here the carbon structure of the embedded nanodiamonds is used to bind. Additionally, the invention increases dramatically the sensitivity of a SPR sensor.

The phenomenon of SPR can be used to detect changes in the refractive index of a surface as a result of the reaction between a sample and target molecule bound to a metallic surface. SPR is the oscillation of the free electron plasma at the surface of a metal boundary. The SPR is affected by the refractive index of the material close to the metallic surface. Using a thin metallic layer, a surface plasmon mode on one side of the layer is able to excite the same mode on the other side of the layer. This is used for sensors by exciting the plasmon on one side and detecting the change of refraction index on the other side by the coupled plasmon.

A key technology to build up a SPR sensor is the binding of the target molecules to the metallic surface. One way is the direct functionalisation of the biomolecules, like DNA, with thiol. These biomolecules will then form a stable covalent binding to the gold layer. Another approach is the formation of complex binding layers on top of the gold layer to bind the molecules indirectly to the gold layer via the surface layer. An alternative approach is the formation of a patterned aminoterpolymer layer. Here UV-light is used to pattern the surface layer on gold to deprotect binding regions for the attachment of biomolecules.

It is the object of the present invention to increase the sensitivity of surface plasmon resonance sensors. This object is solved by the sensor according to claim 1, the use of a sensor according to claim 13, the method for producing a sensor according to claim 14 and the method for detecting target molecules according to claim 15.

Surprisingly, it has been found that the coupling of the plasmon wave on the side towards the light source with the plasmon wave towards the target can be increased if dielectric particles, as e.g. nanodiamonds, are embedded in or bound onto a metallic layer of a surface plasmon resonance sensor. It has furthermore been found that the plasmon wave scatters more strongly on diamonds incorporated in the gold layer which leads to an increased plasmon field. It has furthermore been found that in such an arrangement, the target molecules are bound locally to the region of the enhanced surface plasmons which leads to enhancement of the sensitivity of the sensor.

The sensor according to the invention comprises a sensing layer which comprises or consists of metal. Dielectric particles with a size or maximum diameter of less than or up to 100 nm are embedded in the metallic layer. It is preferred that the sensing layer allows for the excitation of surface plasmon resonance, i.e. the sensor layer can be used for a surface plasmon resonance sensor.

The dielectric particles are preferably diamond particles. They can be fully embedded in the metallic layer, i.e. their complete surface is in contact with the metallic layer, or the particles can alternatively or as well be partially embedded on the surface of the metallic layer, i.e. only a part of their surface is in contact with the metal of the metallic layer.

Preferably, the size or maximum diameter of those particles is between 1 nm and 100 nm, more preferably between 5 nm and 50 nm. Preferably, these ranges are valid for at least 70%, preferably at least 80%, more preferably at least 90%, even more preferably for all of said particles.

The dielectric particles preferably have a metal-non-encapsulated carbon surface, which can be used for the binding with target molecules both directly and indirectly.

The diamond particles can be monocrystalline and/or polycrystalline particles. It is preferred if the diamond particles are embedded in uniform distribution in lateral and/or vertical extension direction of the metallic layer. Thus, it is preferred if the density of the particles is essentially constant in one, more or all directions parallel to the surface of the metallic layer and/or in a direction perpendicular to the surface of the sensor.

The dielectric particles can be incorporated into the metallic film in a random or an ordered way.

The dielectric particles can be located on the external surface of the metallic film and/or fixed in the film.

Preferably, the diamond particles are separated from each other by at least two atomic layers of the metal, preferably at least three atomic layers of the metal and preferably by at least a thickness of metal of the amount of the diameter or size of the particles. Preferably, this condition holds for at least 90%, preferably at least 98%, more preferably all of the embedded diamond particles.

The dielectric particles are preferably separated from each other such that the metallic film is a unified and unbreakable electrically conductive system.

It is preferred if the diamond particles which are partially embedded in and located on the surface of the metallic layer occupy between 1% and 50%, preferably between 40% and 50% of the total surface area of the metallic layer.

In a preferred embodiment of the invention, the sensor comprises particles which are partially embedded. Those partially embedded particles have a surface which is not embedded in the metallic layer. It is preferred if this surface which is not embedded in the metallic layer is functionalized to allow the binding to binding agents non-covalently or covalently. The functionalization can preferably be achieved by biological and/or chemical functionalization, preferably by chemical groups like hydroxyl-, carboxyl-, aldehyde-, carbonyl-, ether-, alcohol-, epoxy-, vinyl-, phenyl- and/or amino-groups, and/or biospecific ligands.

The surface of the particles which is not embedded in the metallic layer can also be functionalized with fluorescent markers.

The binding can be done covalently to any chemical group on the surface of the diamonds (for instance carbonyl group) and/or by electrostatic interaction (for instance between negatively charged carboxyl groups and positively charged amino groups) and/or by the use of biomolecular antibody interaction (for instance biotin-streptavidin).

It is preferred if the metal of the metallic layer comprises or consists of gold and/or silver and/or copper.

It is furthermore preferred if the sensing layer is bound to a substrate layer, which is preferably a glass wafer. Alternatively, the substrate layer can also comprise or consist of copper, iron, steel and/or their alloys with other metals. Preferably, the sensing layer has a thickness between 10 nm and 500 nm, preferably between 20 nm and 400 nm, more preferably between 40 nm and 60 nm.

In an advantageous embodiment, the sensing layer has a non-covered sensing surface with an area of 0.002 $\mu m^2$ and 0.1 $\mu m^2$ for near field surface plasmon resonance detection or between 0.1 $\mu m^2$ and 1 $m^2$ for far field surface plasmon resonance detection.

The ligands for target molecules or substances can directly or indirectly be bound to the surface of the partially embedded diamond particles which is not embedded into the metallic layer.

Said sensor can be used for sensing surface plasmon resonance (SPR). It can be used as chemical sensor and/or biological sensor, e.g. for sensing proteins, DNA, RNA, viruses, cells, bacteria and/or chemical substances, e.g. toxins.

The invention also relates to a method for detecting target molecules or substances, wherein ligands for target molecules or substances are directly or indirectly bound to the surface of the diamond particles which are partially embedded into the surface of the metallic layer. That part of the surface which is not embedded into the metallic layer is contacted with the target molecules and surface plasmon resonance is detected at least before and after contacting said sensor with said target molecules or substances.

The plasmon modes can be excited by known optical techniques.

The dielectric particles form a system of curved closed metal-dielectric interfaces. Under the right conditions for the chosen radius, density and distribution of the dielectric particles in the metallic film, the indicated interfaces lead to an enhancement of the intensity of the plasmon mode which leads to an enhancement of the sensitivity of the sensor.

The sensor can be produced by producing nanoparticles, producing a film of gold containing these nanoparticles by electrochemical deposition and/or chemical deposition and/or spray deposition and applying the film of gold on an optical surface. Preferably, nanoparticles in the film of gold which are located close to the surface of the film of gold are activated by removing gold from the surface so that a part of the surface of the nanodiamonds is not covered by gold anymore.

If necessary, an additional functionalization can be performed on the surface of the nanodiamond particles which is not covered by gold.

In the following, the invention shall be described in more detail by way of examples.

Figure 1:
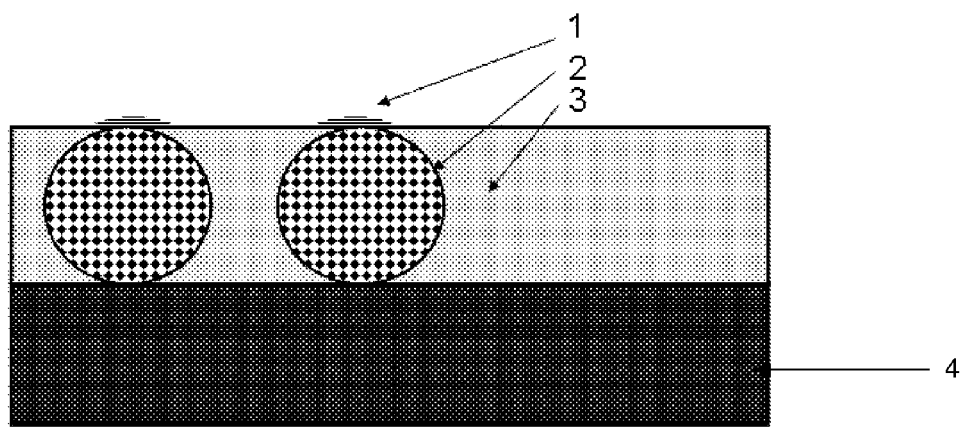
FIG. 1 shows a surface plasmon resonance sensor with diamond particles having a diameter larger than the thickness of the metallic layer.

FIG. 1 shows a surface plasmon resonance sensor according to the present invention. Dielectric nanoparticles 2, e.g. nanodiamonds 2, are embedded in a metallic layer 3, e.g. a gold layer. These diamond particles 2 can have a maximum diameter of less than or up to 100 nm. In FIG. 1, the diamond particles 2 are partially embedded in the metallic layer 3. However, it is also possible that the diamond particles 2 are fully embedded in the metallic layer 3. The size of the dielectric particles 2 can be between 1 nm and 100 nm, wherein at least 70% of the particles fulfil this requirement. Preferably all of the particles fulfil this requirement. If the nanoparticles 2 are nanodiamonds 2, those can be monocrystalline and/or polycrystalline. The particles 2 can be embedded in uniform distribution in lateral and/or vertical extension direction of the metallic layer 3. They can be distributed randomly or ordered. The distance between the nanoparticles 2 is preferably not smaller than two atomic layers of the metal. This is fulfilled preferably for at least 90% of those particles 2.

A part 1 of the surface of the nanodiamonds 2 is not covered with the metal of the metallic layer 3. The surfaces 1 which are not covered with the metal of the metallic layer 3 are together preferably between 1% and 50% of the total surface of the sensor.

Figure 2:
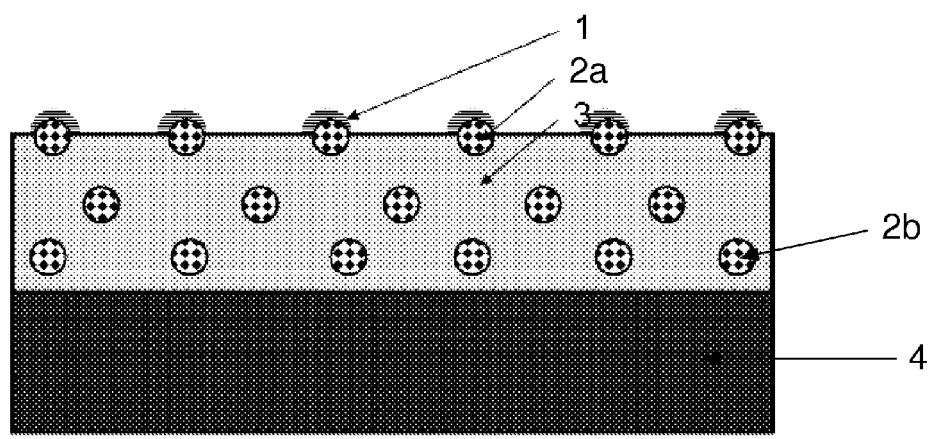
FIG. 2 shows a surface plasmon resonance sensor with diamond particles having a diameter smaller than the thickness of the metallic layer.

FIG. 2 shows a surface plasmon resonance sensor with a plurality of nanodiamonds 2a, 2b, a part 2b of which is fully embedded in the metallic layer 3 and a part 2a of which is partially embedded in the metallic layer 3. Again, the metallic layer 3 is disposed on a substrate for which e.g. can be a glass substrate. It can be seen that the nanodiamond particles 2a, 2b are embedded in uniform distribution in lateral and vertical extension direction of the metallic layer.

Figure 3:
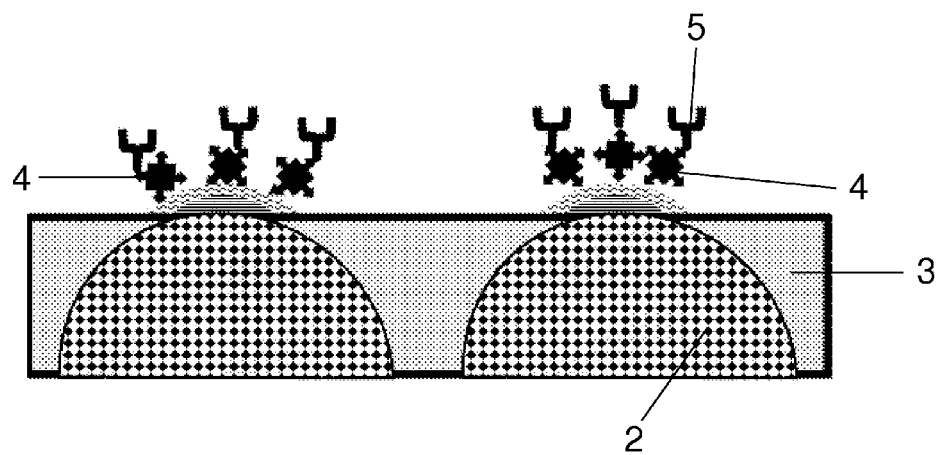
FIG. 3 shows a surface of a surface plasmon resonance sensor with nanodiamonds embedded in a gold layer and being functionalized with a chemical reactive group.

FIG. 3 shows a part of a metallic surface of a surface plasmon resonance sensor according to the present invention where nanodiamonds 2 are embedded in a gold layer and functionalized with chemically reactive groups 6. To the chemically reactive groups 6 biologically reactive molecules 5 (e.g. biotin(1)-streptavidin(2)-antibody(3)-antigen) are bound. The chemically reactive groups 4 are bound to the nanodiamonds 2 on the surface which is not covered by metal of the metal layer 3.

In the following, an example for the production of nanoparticles of a diamond is given. Nanoparticles of diamond can be synthesized using the method of detonation decomposition of the mixture TNT-RDX (50:50) in a closed volume in an oxygenless gas medium. The obtained mixture of condensated products of the detonation was treated by mineral acids and their mixtures at the room and elevated temperatures to dissolve impurities. Nanoparticles of diamond were washed free from acids by distilled water to a neutral reaction of rinsing waters. 10 g of nanodiamond are obtained (yield: 4.5% of the mass of ES, purity: 97%).

The modification of the surface of the nanodiamonds can for example be achieved by two different methods which are described in the following as examples. Firstly, it is possible to carboxylate the surface of a nanodiamond. 5 g of nanodiamond, produced as shown above, were suspended into 250 ml of a mixture of $H_2SO_4$ and $HNO_3$ (in volume relation 4:1) and were boiled with a reflux during 3 hours. The suspension was cooled, nanodiamonds were washed repeatedly with distilled water to a neutral reaction of rinsing waters. 4.5 g of carboxylated nanodiamond are obtained (yield: 90%, purity degree: 99.8%). The functional composition of the surface is analyzed by infra red spectroscopy and clear incidence for carboxylic groups is found. The quantity of carboxylic groups on the diamond surface, determined by the method of potentiometric titration (phone electrolyte—KCl 0.1 M) is found to be 0.4 mg-eq. per gram.

Secondly, an amination of a surface of a nanodiamond is also possible. For example, 5 g of nanodiamond were treated with a mixture of gas fluorine and fluorinated hydrogen at a temperature of more than 150° C., then produced fluorinated diamond was suspended into a solution of diamine from the group $H_2N$—$(CH_2)_n$—$NH_3$, where n=1 . . . 6, and was boiled during 1-6 hours in a protective atmosphere in the presence of catalytic quantities of pyridine. Then diamonds were washed free from excess of reagents with a wateralcohol mixture and were dried at a moderate temperature. 4.7 g of aminated nanodiamonds are obtained (yield: 94%, purity degree: 98%). The functional composition of the surface was proved by infra-red spectroscopy. The quantity of amino-groups, determined by the method of potentiometric titration (phone electrolyte 0.1 M KCL) is found to be 0.32 mg-eq. per gram.

In the following, three examples are given how the film of gold with incorporated particles of nanodiamonds can be produced.

Firstly, electrochemical deposition is possible. The electrolyte used for the deposition contains the complex gold salt $K_2Au(CN_2)$, conductive and buffer addictives. Carboxylated or aminated nanodiamonds were added to get a concentration of 0.01-5 g/l. The mixture was carefully stirred and homogenized using ultrasound. The deposition of the golden film was performed at a cathode current density of 0.05 to 5 $A/dm^2$, substrate (cathode) was made of polished copper flat wafer with a measured root-mean-square roughness of $R_z$=10 nm. The obtained golden film with incorporated particles of nanodiamond has a thickness from 10 to 500 nm.

Secondly, chemical deposition is possible. To a solution of chemical gliding, containing the complex salt of gold $K_2Au(CN_2)$ and reducing agent, as well as buffer and stabilizing additives, carboxylated or aminated nanodiamonds were added. The used concentration was 0.01 to 1.0 g/l. The solution was carefully stirred and homogenized using ultrasound. The deposition of the coating was performed at a temperature of 70 to 98° C. on a steel polished wafer. The root-mean-square roughness of the wafer was measured to be $R_z$=10 nm. The obtained golden film with incorporated particles of nanodiamond has a thickness from 10 to 500 nm.

Furthermore, spray deposition is possible. Here, a target fabricated from gold with incorporated particles of nanodiamond is deposited on a polished glass wafer.

In the following, an example for applying the film on the optical surface is given. The golden film obtained in accordance with the previously described method was treated with a solution of a mineral acid (nitric or hydrochloric or sulfuric acids). The substrates, fabricated from a non-noble material such as copper, copper alloy, steel, etc., dissolves under these conditions. The free golden film was washed with distilled and deionized water and afterwards air dried.

The free film of gold with incorporated particles of nanodiamond is cemented with the use of suitable optical glue on the polished surface of the glass wafer, avoiding deformation and damages of the film.

An activation of nanoparticles incorporated into the metallic film can for example be achieved as follows. Firstly, the gold has to be removed from the nanodiamonds which are located on the surface of the metal layer. This can be done as follows. The metallic film with incorporated particles, fixed on the glass substrate, is treated by short-time dipping into the mixture $HCl:HNO_3$=3:1 at room temperature, whereupon it is carefully washed with water and dried.

It is possible to additionally functionalize the surface of the incorporated particles of the diamond located in the surface layer of the metallic film. This can be done e.g. as follows.
i) a wafer fabricated as described above is treated with an oxidative mixture ($HNO_3$:$H_2SO_4$), and in this process the carboxylated surface of nanoparticles is obtained;
ii) analogues wafer is treated with amination reagents and in this process the aminated surface of nanodiamond is obtained.

In the following, some particle properties of nanodiamonds are shown as an example.

| Quantity | Unit | UDD1 | UDD2 |
|---|---|---|---|
| Average size of the primary particles | nm | 4-6 | 6-8 |
| Average size of the particle aggregates | nm | 20-30 | 30-50 |
| specific surface areal | $m^2/g$ | 330 | 215 |
| electrokinetic (Z-) Potential (pH 7, 25 C.) | mV | −35 | −22 |
| content of non-burnable additives (ashes) | % | 0.5 | 0.3 |

A characterisation of the produced nanodiamond particles can e.g. be done by fluorescence spectroscopy. The above-mentioned probes UDD1 and UDD2 show a green fluorescence upon excitation with blue light at 467 nm. The spectrum shows a maximum at 508 nm where the width of the peak is about 20 nm. The spectra of those probes are comparable, the intensity and thus the height of the quantum efficiency however differs by a factor of about 1.6. The intensity differences between the values for the basis line and the peak were about 190000 for UDD1 and 120000 for UDD2. The efficiency of the excitation is dependent on the wavelength of the light. In this example, a measurement was done in the region from 450 to 490 nm wherein the intensity varied by a factor of 2.5.

A characterisation of the nanoparticles is also possible by UV-VIS-analysis. Here, probes with nanodiamonds showed an exponential increase of absorption with decreasing wavelength. With increasing concentration of diamonds, higher extinctation values can be seen.

The invention claimed is:

1. A sensor comprising a sensing layer,
   wherein the sensing layer is a metallic layer,
   wherein diamond particles with a size or maximum diameter of less than or up to 100 nm are fully embedded in the metallic layer and partially embedded on the surface of the metallic layer,
   wherein the diamond particles are embedded in uniform distribution in lateral and vertical extension direction of the metallic layer so that the density of the particles is constant in all directions parallel to the surface of the metallic layer and in a direction perpendicular to the surface of the sensor, and
   wherein the diamond particles partially embedded in and located on the surface of the metallic layer occupy between 1% and 50% of the total surface area of the metallic layer.

2. The sensor according to claim 1, wherein the sensing layer is a surface plasmon resonance sensor layer.

3. The sensor according to claim 1, wherein the diamond particles have at least one of the following properties:
   a) their size or maximum diameter is between 1 nm and 100 nm, wherein this range is valid for at least 70% of all of said diamond particles; or b) the diamond particles are monocrystalline and/or polycrystalline particles; the diamond particles are separated from each other by no less than two atomic layers of the metal, for at least 90% of the embedded diamond particles.

4. The sensor according to claim 1, wherein the surface of the partially embedded diamond particles, which is not embedded in the metallic layer, is functionalized in order to bind non-covalently or covalently to binding agents, by chemical groups like hydroxyl-, carboxyl-, aldehyde-, carbonyl-, ether-, alcohol-, epoxy-, vinyl-, phenyl-and/or amino-groups, and/or bio specific ligands.

5. The sensor according to claim 1, wherein the surface of the partially embedded diamond particles, which is not embedded in the metallic layer, is functionalized with fluorescent markers.

6. The sensor according to claim 1, wherein the metal of the metallic layer is gold and/or silver and/or copper.

7. The sensor according to claim 1, wherein the sensing layer is bound to a substrate layer, the substrate layer being a glass wafer or a substrate layer comprising copper, iron, steel or their alloys with other metals.

8. The sensor according to claim 1, wherein the sensing layer has a thickness between 10 nm and 500 nm.

9. The sensor according to claim 1, wherein the sensing layer has a sensing surface not covered by the metallic layer with an area of 0.002 $\mu m^2$ and 0.1 $\mu m^2$ for near field surface plasmon resonance detection or between 0.1 $\mu m^2$ and 1 $m^2$ for far field surface plasmon resonance detection.

10. The sensor according to claim 1, wherein ligands for target molecules or substances are directly or indirectly bound to the surface of the diamond particles partially embedded into the surface of the metallic layer, which is not embedded into the metallic layer.

11. A surface plasmon resonance (SPR) sensor, wherein it comprises a sensor according to claim 1.

12. A method comprising:
providing a sensor comprising a sensing layer, wherein the sensing layer is a metallic layer, wherein diamond particles with a size or maximum diameter of less than or up to 100 nm are fully embedded in the metallic layer and partially embedded on the surface of the metallic layer, wherein the diamond particles are embedded in uniform distribution in lateral and vertical extension direction of the metallic layer so that the density of the particles is constant in all directions parallel to the surface of the metallic layer and in a direction perpendicular to the surface of the sensor, wherein the diamond particles partially embedded in and located on the surface of the metallic layer occupy between 1% and 50% of the total surface area of the metallic layer; and sensing surface plasmon resonance (SPR), and/or as chemical sensor and/or biological sensor, e.g. for sensing proteins, DNA, RNA, viruses, cells, bacteria or chemical substances, e.g. toxins.

13. A method for producing a sensor comprising a sensing layer,
wherein the sensing layer is a metallic layer, wherein diamond particles with a size or maximum diameter of less than or up to 100 nm are fully embedded in the metallic layer and partially embedded on the surface of the metallic layer, wherein the diamond particles are embedded in uniform distribution in lateral and vertical extension direction of the metallic layer so that the density of the particles is constant in all directions parallel to the surface of the metallic layer and in a direction perpendicular to the surface of the sensor, wherein the diamond particles partially embedded in and located on the surface of the metallic layer occupy between 1% and 50% of the total surface area of the metallic layer;
wherein when diamond nanoparticles are produced, a film of gold incorporating the diamond nanoparticles is produced by electrochemical deposition and/or chemical deposition and/or spray deposition, and the film of gold is applied on an optical surface, and
wherein preferably, the diamond nanoparticles are activated by removing gold from nanoparticles located near a surface of the film of gold and wherein the diamond nanoparticles are further functionalized.

14. A method for detecting target molecules or substances, wherein a sensor comprising a sensing layer, wherein the sensing layer is a metallic layer, wherein diamond particles with a size or maximum diameter of less than or up to 100 nm are fully embedded in the metallic layer and partially embedded on the surface of the metallic layer, wherein the diamond particles are embedded in uniform distribution in lateral and vertical extension direction of the metallic layer so that the density of the particles is constant in all directions parallel to the surface of the metallic layer and in a direction perpendicular to the surface of the sensor, wherein the diamond particles partially embedded in and located on the surface of the metallic layer occupy between 1% and 50% of the total surface area of the metallic layer; and wherein ligands for target molecules or substances are directly or indirectly bound to the surface of the diamond particles partially embedded into the surface of the metallic layer, which is not embedded into the metallic layer, is contacted with said target molecules and surface plasmon resonance is detected at least before and after contacting said sensor with said target molecules or substances.

* * * * *